United States Patent
Kim et al.

(10) Patent No.: US 9,657,259 B2
(45) Date of Patent: *May 23, 2017

(54) CELL CULTURE FLASK AND THE CELL CULTURE DEVICE HAVING IT

(71) Applicant: Corestem Co., Ltd., Chungcheongbuk-do (KR)

(72) Inventors: Kyung Suk Kim, Seoul (KR); Jai Jun Choung, Seoul (KR)

(73) Assignee: Corestem Co., Ltd., Gangnae-myeon, Chungcheongbuk-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/701,783

(22) Filed: May 1, 2015

(65) Prior Publication Data

US 2015/0232795 A1  Aug. 20, 2015

Related U.S. Application Data

(62) Division of application No. 12/745,127, filed as application No. PCT/KR2008/007035 on Nov. 28, 2008, now abandoned.

(30) Foreign Application Priority Data

Nov. 30, 2007  (KR) .......................... 10-2007-0123912

(51) Int. Cl.
*C12M 1/24* (2006.01)
*C12M 1/00* (2006.01)

(52) U.S. Cl.
CPC ............ *C12M 23/08* (2013.01); *C12M 23/22* (2013.01); *C12M 23/38* (2013.01); *C12M 29/00* (2013.01); *C12M 29/26* (2013.01)

(58) Field of Classification Search
CPC ...... C12M 23/08; C12M 23/22; C12M 23/38; C12M 29/00; C12M 29/26
(Continued)

(56) References Cited

U.S. PATENT DOCUMENTS 4,307,193 A  12/1981  Iizuka
4,335,215 A  6/1982  Tolbert et al.
(Continued)

FOREIGN PATENT DOCUMENTS

JP  2005-095015 A  4/2005
KR  1020020065128 A  8/2002

OTHER PUBLICATIONS

Isayeva et al., "Advanced methods of adenovirus vector production for human gene therapy: roller bottles, microcarriers, and hollow fibers," Bioprocessing J. Sep./Oct. 75-81 (2003).
(Continued)

*Primary Examiner* — Gautam Prakash
(74) *Attorney, Agent, or Firm* — Clark & Elbing LLP; Susan M. Michaud

(57) ABSTRACT

The present invention relates to a cell culture flask for culturing a cell using a culture solution, particularly to a cell culture flask for culturing a cell without any contamination, to automatically introduce and discharge the culture solution or gases and to be stacked in turn, and a cell culture device having the same. The present invention provides a cell culture flask comprising a culture space; one or more culture solution inlet ports; one or more culture solution outlet ports; and one or more gas inlet ports, wherein the cell culture flask is made airtight and formed of a transparent material so that a user can see an internal portion of the cell culture flask, and a cell culture device having the same.

6 Claims, 15 Drawing Sheets

(58) Field of Classification Search
USPC ......... 435/303.1, 304.3, 293.1, 297.1, 297.5, 435/305.1, 305.2, 307.1
See application file for complete search history.

(56) References Cited

U.S. PATENT DOCUMENTS

| | | | |
|---|---|---|---|
| 4,639,422 | A | 1/1987 | Geimer et al. |
| 5,350,080 | A | 9/1994 | Brown et al. |
| 5,871,699 | A | 2/1999 | Ruggeri |
| 6,197,574 | B1 | 3/2001 | Miyamoto et al. |
| 7,682,823 | B1 | 3/2010 | Runyon |
| 9,057,715 | B2 * | 6/2015 | Kim ................. C12M 23/08 |
| 2002/0045861 | A1 | 4/2002 | Tribe |
| 2006/0128005 | A1 | 6/2006 | Hasegawa et al. |
| 2006/0223155 | A1 | 10/2006 | Streeter |
| 2008/0273914 | A1 | 11/2008 | Hamada |

OTHER PUBLICATIONS

Terashima et al., "Effects of sugar concentration on recombinant human alpha(1)-antitrypsin production by genetically engineered rice cell," Biochem Eng J. 6(3):201-205 (2000).

International Search Report for International Patent Application No. PCT/KR2008/007035, dated Aug. 26, 2009 (3 pages).

* cited by examiner

CELL CULTURE FLASK AND THE CELL CULTURE DEVICE HAVING IT

BACKGROUND OF THE INVENTION

Field of the Invention

The present invention relates to a cell culture flask for culturing a cell using a culture solution, particularly to a cell culture flask enabling to culture a cell without any contamination, to automatically introduce and discharge the culture solution or gases and to be stacked in turn, and a cell culture device having the same.

Background of Technique

Cell culture comprises aseptically cutting off tissue sections from multicellular organisms and providing nutritive components to them, followed by incubation for cell proliferation in a vessel. The tissues of plants can be immortally proliferated.

A cell culture method includes a coverglass method, a flask method, a rotating tube method and the like. Generally, endosperm, leukocyte or spleen extracts are used to promote the growth of cultured tissues while its essential materials are not clearly elucidated yet. Recently, an antibiotic or an eagle culture solution containing vitamins and amino acids are often used.

The tissue culture permits a single cell to culture to a cell population, a small organ or a plant tissue.

The culture of living cells in a test tube is performed for various purposes, for example, recovery of additional by-products generated by cellular metabolisms, preparation of virus vaccines, culture of cells to fabricate an artificial organ, production of medicines by manipulating genes of an animal cell, breeding of a plant by cell fusion.

In general, the culture of animal cells requires culture media containing nutrients such as amino acids, sugars, inorganic nutrients and vitamins, and their culture conditions are complicated. The plant cells have high viability due to their photosynthesis capabilities compared with animal cells, and thus it is easy to culture them but their proliferation rate is slow.

For efficient culture of the animal cells, the cell culture methods according to cell properties have been intensively studied. As results, the cell culture methods based on the characteristics of each cell such as hybridomas and embryonic stem cells were developed and widely utilized. However, a mass culture method of adhesive cells such as fibroblastoids and epithelial-like cells is not well established yet, which has some problems that its culture yield is so low and its prolonged culture is difficult.

A predetermined space for culturing cells, a culture solution for supplying nutritions to them, and various gases are required for cell culture. Certainly, it is also the same in the plant cells.

Particularly, the culture solutions and various gases are introduced into the culture space and used for culturing cells, following the periodical exchange with new ones to maintain the cell tissues in a fresh condition.

Therefore, a cell culture device is essentially provided with a construction to supply and discharge the culture solutions and various gases continuously and smoothly.

For the exchange of the culture solutions, a method utilizes a pipet to suck the culture solutions, to introduce and discharge them into the culture space. However, it is inefficient due to a possibility involving the cells in discharged culture solution and a difficulty of smooth exchange of the culture solution.

According to another conventional method, there is a method that the culture space is provided with an inlet port at one side thereof through which a predetermined amount of culture solution is introduced by an automatic or manual system, and with an outlet port at the other side thereof through which the culture solution used is discharged in the same manner.

In this method, a foreign substance could be introduced through the inlet port or the outlet port, thereby contaminating the cells. This method is also inconvenient because a user always participates in operation of the cell culture device. Furthermore, the mass cell culture is impossible due to the low efficiencies of the surface area caused from the use of the single device.

DETAILED DESCRIPTION OF THE INVENTION

It is an object of the present invention to provide a cell culture flask for mass cell culture which can culture a cell without any contamination, can automatically introduce and discharge the culture solution or gases and can be stacked in turn, and a cell culture device having the same.

To achieve the above object, the present invention provides a cell culture flask for culturing a cell using a culture solution and various gases, comprising: a culture space with a predetermined area for culturing the cell; one or more culture solution inlet ports for introducing the culture solution or the cell into the culture space; one or more culture solution outlet ports for discharging the culture solution or the cell supplied to the culture space; and one or more gas inlet ports for introducing the various gases into the culture space, wherein the cell culture flask is made airtight and formed of a transparent material so that a user can see an internal portion of the cell culture flask.

Preferably, the culture solution inlet port and the culture solution outlet port comprises: a cylindrical tube member which is outwardly protruded to receive the culture solution and formed with a hole through which the culture solution is flowed; a piston member which is disposed to be reciprocated in the cylindrical tube member; a connection member of which one end is connected with the piston member and the other end is connected with an external power supply part; and a sealing member which is attached to an end of the cylindrical tube member and formed with an opening through which the connection member can be reciprocated.

Preferably, the power supply part comprises a detachable motor operated by electric power supplied through a cable from an outside, and the connection member comprises a linear rod or a lead screw.

Preferably, the cell culture flask further comprises one or more gas outlet ports for discharging the various gases supplied to the culture space.

Preferably, the cell culture flask further comprises one or more foreign substance inlet ports for introducing a foreign substance.

Preferably, the foreign substance inlet port is opened and closed by a cap-type stopper.

Preferably, the cell culture flask is formed into a cylindrical shape with a predetermined height and comprises the culture space at a center portion thereof, and the culture solution inlet and outlet ports, the gas inlet and output ports, and the foreign substance inlet ports are formed along a side surface of the cell culture flask.

To achieve another object, the present invention provides a cell culture device, comprising: a cell culture flask comprising a culture space for culturing cells, a culture solution inlet port for introducing a culture solution or the cell into the culture space, a culture solution outlet port for discharging the culture solution or the cell supplied to the culture space, and a gas inlet port for introducing various gases into the culture space, wherein the cell culture flask is made airtight and formed of a transparent material to observe its internal portion; an injection unit for supplying the culture solution to the cell culture flask through a culture solution inlet port of the cell culture flask; a collection unit for collecting the culture solution to outside of the cell culture flask through a culture solution outlet port of the cell culture flask; and a cell culture flask receiving portion comprising an injecting part and a collecting part to be equipped with the injection unit and the collecting unit, a plate-shaped connecting part which separately connects an upper part or a lower part of the collecting part and the injecting part, and a supporting part which is provided at the connecting part, wherein the cell culture flask is disposed between the connecting parts of the cell culture flask receiving portion.

Preferably, the cell culture device further comprises one or more gas outlet ports for discharging the various gases supplied to the culture space.

Preferably, the cell culture device further comprises one or more foreign substance inlet ports for introducing the foreign substance.

Preferably, the foreign substance inlet port is opened and closed by a cap-type stopper.

Preferably, the cell culture flask is formed of a cylindrical shape with a predetermined height comprising the culture space at a center portion thereof, and the culture solution inlet and outlet ports, the gas inlet and output ports, and the foreign substance inlet ports are formed along the side surface of the cell culture flask.

Preferably, the transparent material comprises a plastic such as lexan and acryl or a tempered glass.

Preferably, the injection unit and the collection unit comprises: a syringe part comprising a power supply part; a culture solution storing part which is connected with the syringe part and stores the culture solution; a contact part which is connected with the culture solution storing part and contacted with the culture solution inlet port or the culture solution outlet port of the cell culture flask to flow the culture solution; a piston member which is disposed to be reciprocated in the culture solution storing part; and a connection member of which one end is connected with the piston member and the other end is connected with the power supply part, wherein the injection unit and the collection unit are formed into an injector as a whole.

Preferably, the connection member comprises a linear rod or a lead screw.

Preferably, the power supply part is a detachable motor which is operated by electric power supplied through a cable from an outside.

Preferably, the injecting part and the collecting part of the cell culture flask receiving portion are radially or vertically connected with an outer surface of the cell culture flask.

Preferably, the cell culture flask receiving portion is formed of a plastic such as lexan and acryl or a stainless steel.

According to the cell culture flask and the cell culture device having the same by the present Examples described above, particularly an airtight culture space permits to culture the cells without any contamination. The present invention also enables to automatically supply and discharge the culture solution and various gases, and allows the cells to mass-produce, thereby increasing space efficiency.

DETAILED DESCRIPTION OF MAIN ELEMENTS

| | |
|---|---|
| 100, 200, 310, 410: cell culture flask | |
| 300, 400: cell culture device | 110, 210: culture space |
| 120, 220, 320, 420: culture solution inlet port | |
| 130, 230, 330, 430: culture solution outlet port | |
| 140, 240, 340, 440: gas inlet port | |
| 150, 250, 350, 450: gas outlet port | |
| 160, 260, 360, 460: foreign substance inlet port | |
| 165, 265, 365, 465: stopper | |
| 222, 232: cylindrical tube member | 223, 233: piston member |
| 224. 234: hole | 225, 235: connection member |
| 226, 236: sealing member | 228, 238: power supply part |
| 370, 470: cell culture flask receiving portion | |
| 371, 471: injecting part | 372, 472: collecting part |
| 373, 473: connecting part | 375, 382: syringe part |
| 376, 383: culture solution storing part | 377, 384: contact part |
| 378, 385: piston member | 379, 386: connection member |
| 374: injection unit | 381: collection unit |

Examples

The objects, characters or other advantages of this invention described above will become apparent to those skilled in the art by explaining the preferable Examples of the present invention in detail referring to the appended drawings. The cell culture flask and the cell culture device having the same according to the Examples of the present invention will be described in further detail together with the appended claims and drawings below.

Figure 1:
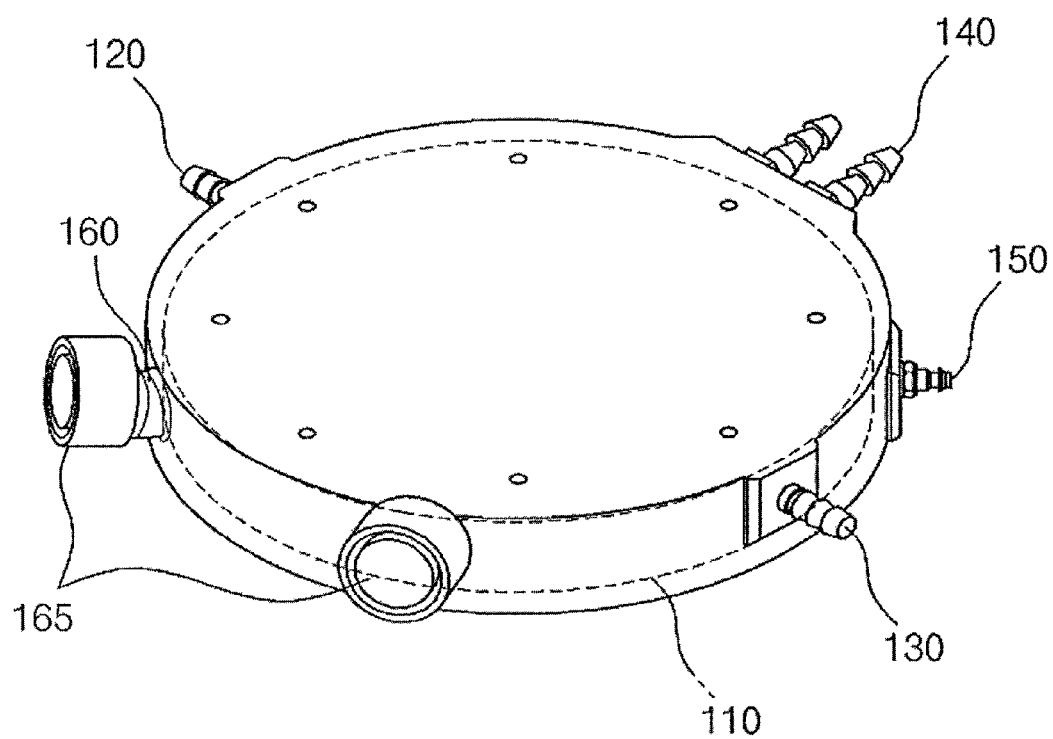
FIG. 1 represents a perspective view of a cell culture flask (100).
Figure 2:
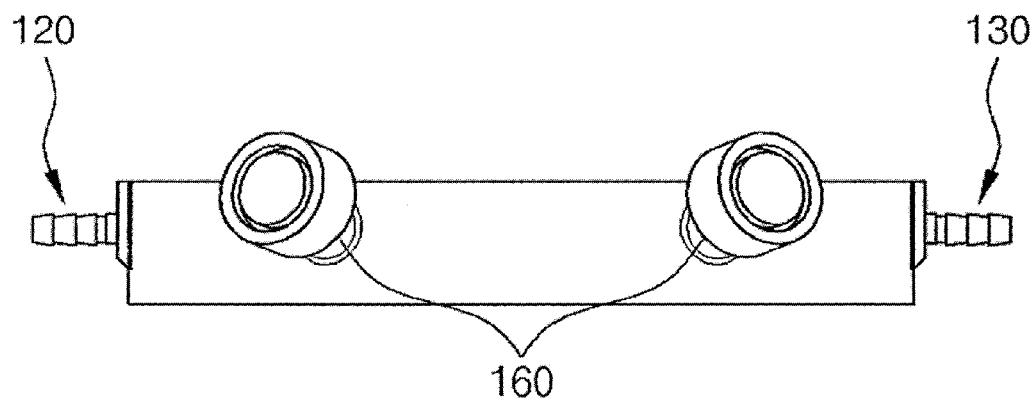
FIG. 2 is a front view of the cell culture flask (100) of FIG. 1.

FIG. 1 represents a perspective view of a cell culture flask according to an embodiment of the present invention, and FIG. 2 is a front view of the cell culture flask of FIG. 1.

Given to FIGS. 1-2, the cell culture flask (100) according to an embodiment of the present invention includes a culture space (110) with a predetermined space for culturing cell, a culture solution inlet port (120) for introducing a culture solution or the cell into the culture space (110), a culture solution outlet port (130) for discharging the culture solution or the cell from the culture space (110), and a gas inlet port (140) for introducing the various gases into the culture space (110).

If necessary, the culture solution inlet port (120), the culture solution outlet port (130) and the gas inlet port (140) may be further provided in plural.

The cell culture flask (100) may further includes a gas outlet port (150) for discharging the various gas introduced into the culture space (110), and a foreign substance inlet port (160) for introducing a foreign substance.

And if necessary, the gas outlet port (150) and the foreign substance inlet port (160) may be provided in plural.

Generally, the culture space (110) existed inside the cell culture flask (110) has a flat surface without irregular or inclined portions. In some cases, a part of the culture space (110) may possess an inclined surface.

The culture solution inlet port (120) and outlet port (130) are formed to be protruded from an outer surface of the cell culture flask (100) and to constitute a narrow end, preventing the foreign substance from being introduced into the culture space (110) where the culture solution is not flowed through the culture solution inlet port (120) and outlet port (130).

Preferably, in the culture solution inlet port (120) and outlet port (130) disposed to be adjacent to each other, the culture solution is flowed into the culture solution inlet port (120) which is opened to supply it. The culture solution inlet port (120) and outlet port (130) can be disposed to be adjacent to each other where there is no such possibility.

The gas inlet port (140) may be provided in plural separately from the culture solution inlet port (120) and outlet port (130). In the animal cells cultured in the cell culture flask, $O_2$ supply is needed and $CO_2$ supply is required in the plant cells. These gases can be supplied through the gas inlet port (120). Meanwhile, $N_2$ or other gases can be supplied.

Normal gas supply and discharge is essential to maintain the cell cultured in the cell culture flask in a fresh condition. Therefore, the gas outlet port (150) to discharge the gas supplied inside the cell culture flask to an outside is provided. In a disposable cell culture flask (100), since a predetermined amount of culture solution and gas is supplied to the cell culture flask and then grown cells are harvested, the gas outlet port (150) is not separately needed. In a cell culture flask (100) used repeatedly, the gas outlet port (150) is required to maintain the cells in the fresh condition and an internal portion of the cell culture flask (100) in a clean condition.

The gas outlet port (150) is used to supply the gas excessive or to remove gas generated from the cells per se.

To grow the cells normally, the foreign substance inlet port (160) for supplying a foreign substance can be separately provided. The foreign substance inlet port (160) is provided with a cap-type stopper (165) for opening and closing.

The stopper (165) may be a general rubber stopper. The collecting tools such as a pipet can be used where the foreign substance is introduced through the foreign substance inlet port (160).

A user can collect a necessary amount of cells through the foreign substance inlet port (160). The pipet can be also used.

The cell culture flask (100) shown in FIGS. 1-2 is made airtight as a whole and formed of a transparent material to observe its internal portion. Therefore, the researcher can observe a growth level of the cells from the outside.

The transparent material includes a transparent plastic such as lexan and acryl or other plastics. Preferably, the transparent material is a non-fragile tempered glass.

The cell culture flask (100) represented in FIGS. 1-2 has a cylindrical shape, but it is possible to be other shapes such as a rectangular parallelepiped structure and a polyhedral structure. On the other hand, the cell culture flask (100) formed of the cylindrical shape has a wide culture space and a high strength against external impact and is facilely moved due to the absence of its corner portion.

The present cell culture flask (100) is formed into the cylindrical shape with a predetermined height comprising the culture space at a center portion thereof. The culture solution inlet ports (120) and outlet ports (130), the gas inlet ports (140) and output ports (150), and the foreign substance inlet port (160) are formed along a side surface of the cell culture flask (100).

This structure represents an example of the cell culture flask (100). As described above, the cell culture flask (100) may have various structures, e.g., the polyhedral structure.

Figure 3:
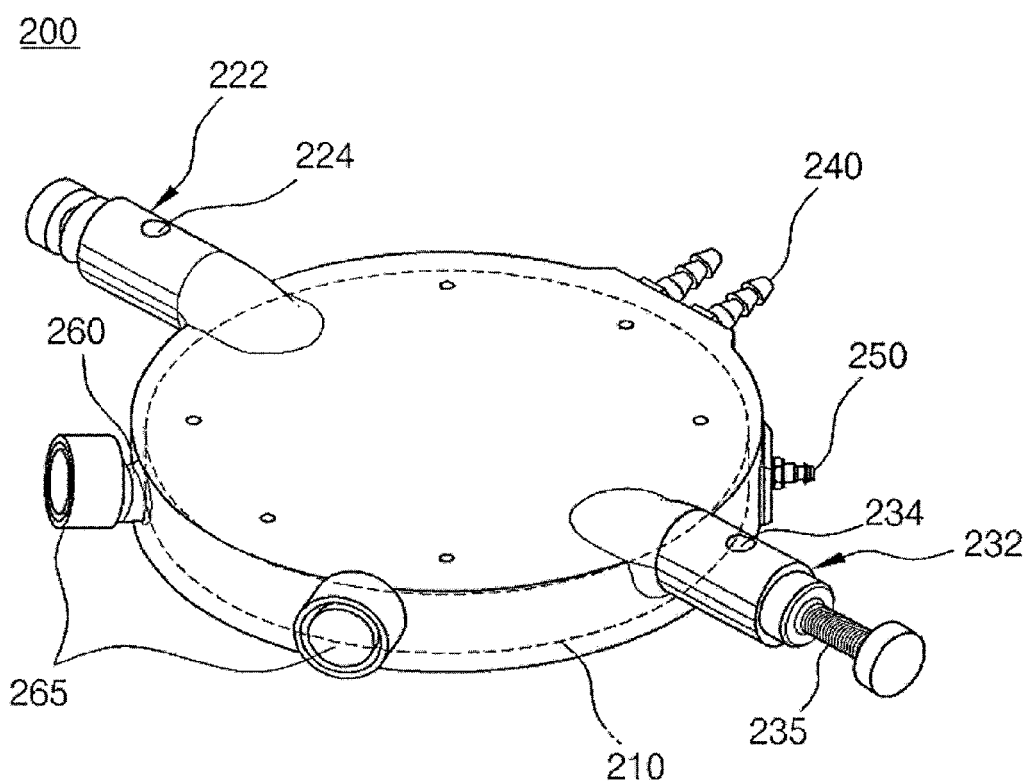
FIG. 3 represents a perspective view of a cell culture flask (200).
Figure 4:
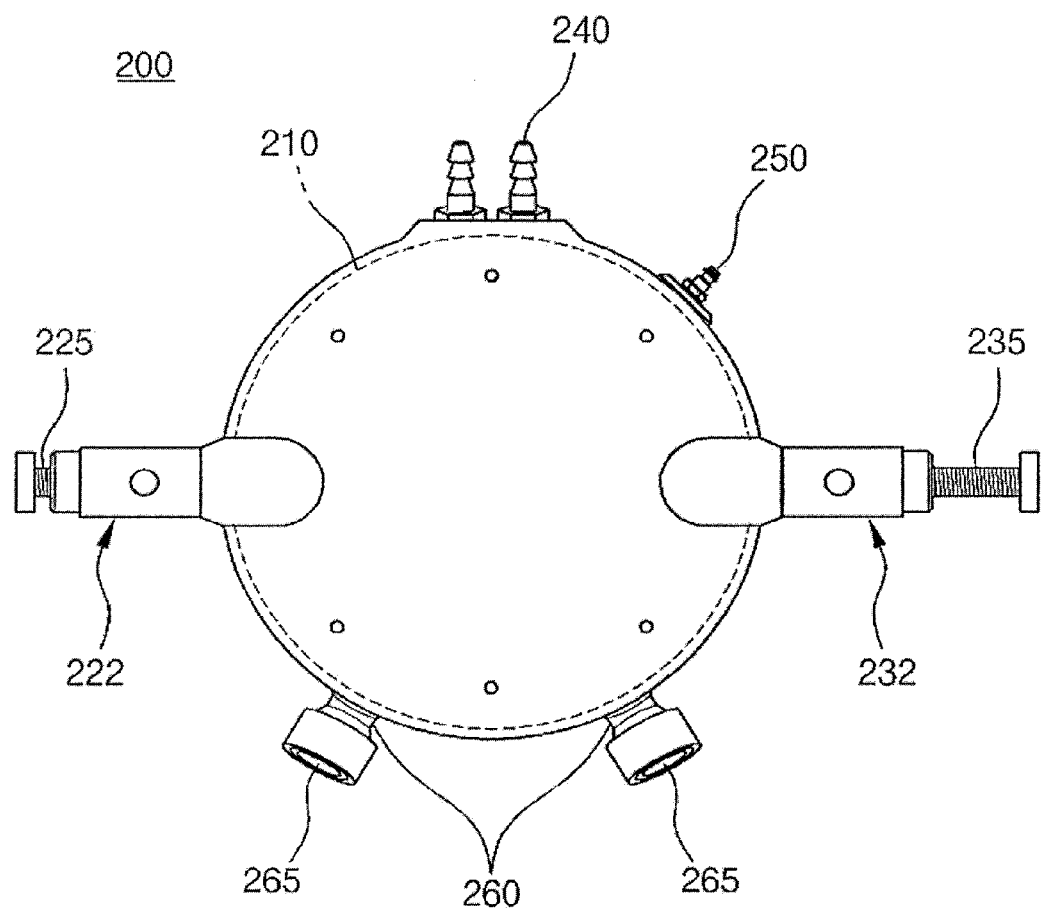
FIG. 4 is a plane view of the cell culture flask (200) of FIG. 3.
Figure 5:
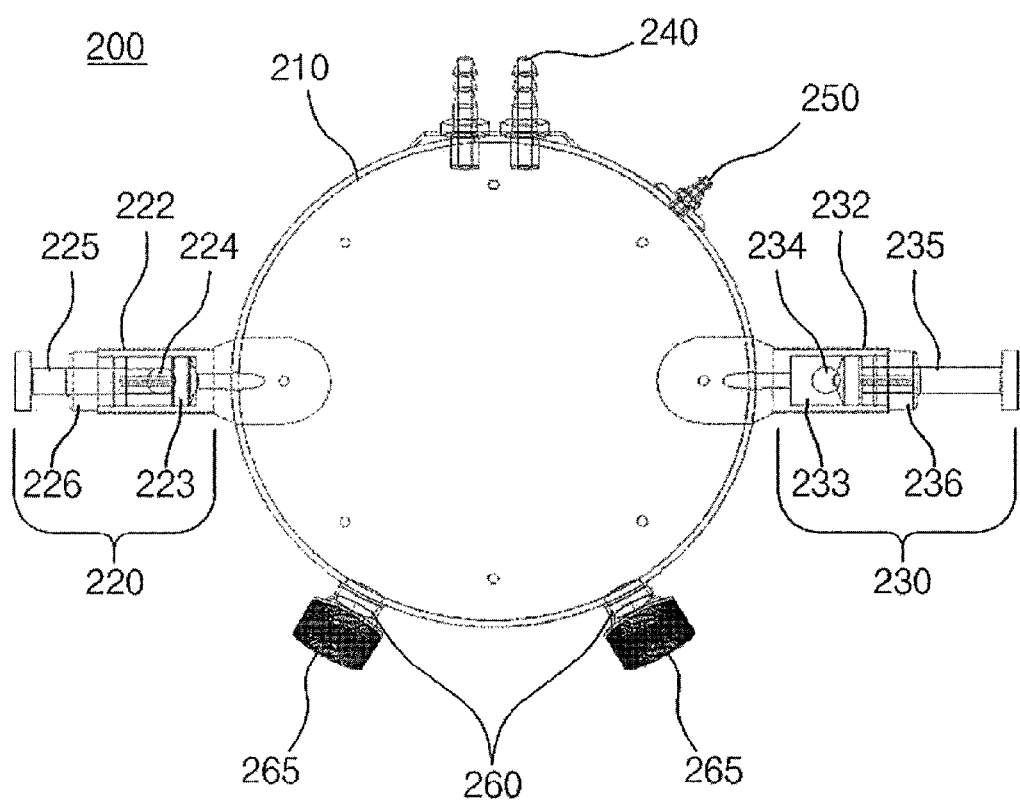
FIG. 5 is a perspective plane view of the cell culture flask (200) of FIG. 3.
Figure 6:
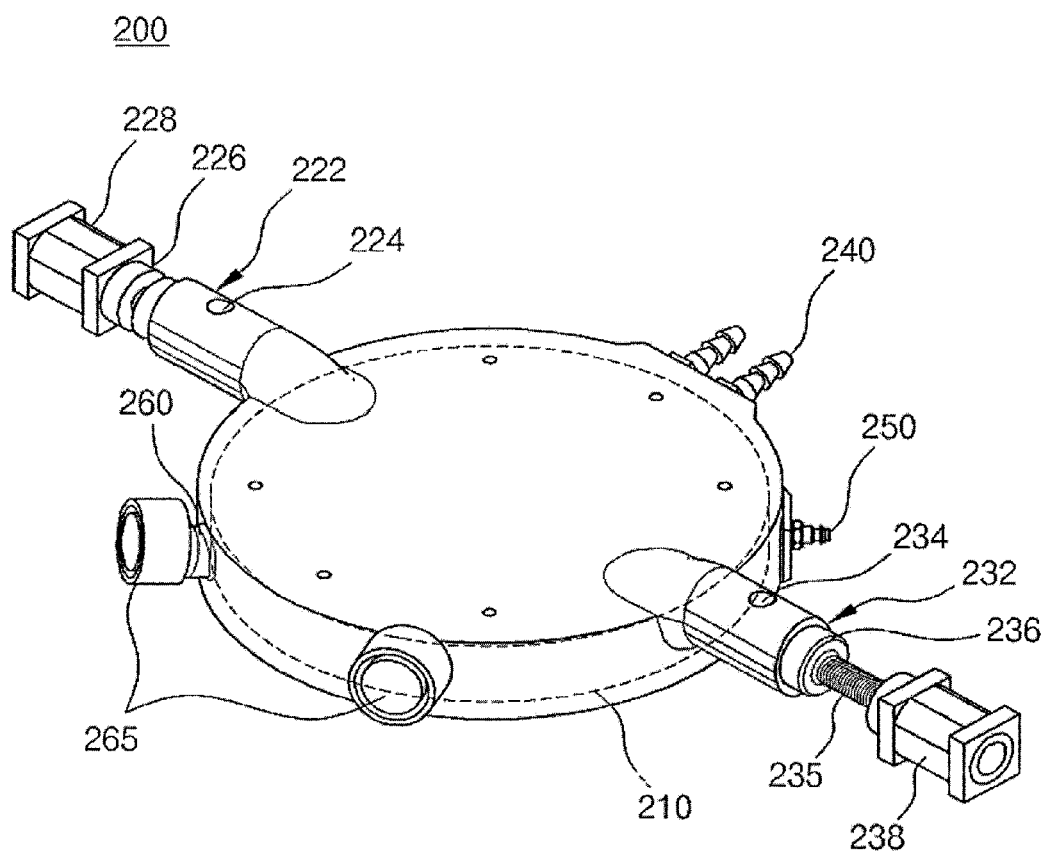
FIG. 6 represents a perspective view of the cell culture flask (200) of FIG. 3, in which a motor is installed.
Figure 7:
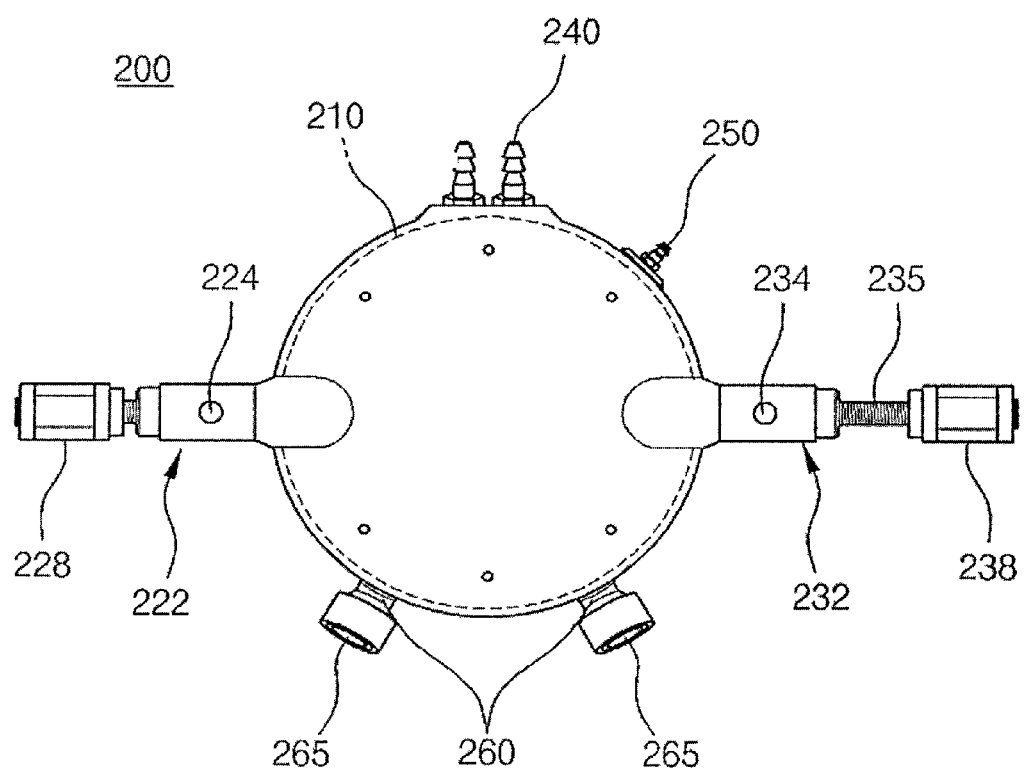
FIG. 7 is a front view of cell culture flask (200) of FIG. 6.

FIG. 3 represents a perspective view of a cell culture flask (200) according to another embodiment of the present invention, and FIG. 4 is a plane view of the cell culture flask (200) of FIG. 3. FIG. 5 is a perspective plane view of the cell culture flask (200) of FIG. 3, FIG. 6 represents a perspective view of the cell culture flask (200) of FIG. 3, in which a motor is installed, and FIG. 7 is a front view of cell culture flask (200) of FIG. 6.

Given to FIGS. 3-7, the cell culture flask (200) according to another embodiment of the present invention includes a culture space (210) with a predetermined area for culturing cell, a culture solution inlet port (220) for introducing a culture solution or the cell into the culture space (210), a culture solution outlet port (230) for discharging the culture solution or the cell from the culture space (210), and a gas inlet port (240) for introducing the various gases into the culture space (210).

If necessary, the culture solution inlet port (220), the culture solution outlet port (230) and the gas inlet port (240) may be provided in plural.

The culture solution inlet port (220) and the culture solution outlet port (230) include a cylindrical tube member (222, 232) which is outwardly protruded to receive a culture solution and formed with a hole (224, 234) through which the culture solution is flowed, a piston member (223, 233) which is disposed to be reciprocated in the cylindrical tube member (222,232), a connection member (225, 235) of which one end is connected with the piston member (223, 233) and the other end is connected with an external power supply part, and a sealing member (226, 236) which is attached to an end of the cylindrical tube member (222, 232) and formed with an opening through which the connection member (225, 235) can be reciprocated.

The power supply part shown in FIGS. 6-7 includes a detachable motor (228, 238) operated by electric power supplied through a cable from an outside, or other devices such as an electromotor or a pump.

The connection member (225, 235) includes a linear rod which is simply reciprocated, or a lead screw which is reciprocated during rotation. However, it is operated by rotational force of the motor in the lead screw used as the connection member (225, 235).

Instead of using the power supply part like the motor, a user can grasp an outer end portion of the connection member (225, 235) and apply force to move the connection member (225, 235). The user can directly operate the connection member (225, 235) to extract the culture solution or the cells where the purpose of the cell culture is not to produce cells massively, but just to obtain a small amount of particular cells for an experiment.

For injection of the culture solution through the culture solution inlet port (220), the culture solution is introduced through the hole (224) formed in the cylindrical tube member (222) and then applies force to the connection member (225) manually or using the motor so that the piston member (223) is pushed toward the cell culture flask (200) and the culture solution or the cells are pushed into the inside of the cell culture flask (200) by the applied force.

On the contrary, to extract the culture solution through the culture solution outlet port (230), the piston member (233) is pulled toward outside the cell culture flask (200) by applying force to the connection member (235) in a manual or motor manner. Thus, the culture solution or the cells inside the cell culture flask (200) are discharged to a space between the piston member (233) and the cylindrical tube member (232), whereby the user can extract the culture solution or the cell through the hole (234) of the cylindrical tube member (232).

The cell culture flask (200) further includes a gas outlet port (250) for discharging the various gases introduced into the culture space (210), and a foreign substance inlet port (260) for introducing a foreign substance.

If necessary, the gas outlet port (250) and the foreign substance inlet port (260) may be provided in plural.

Preferably, the culture solution inlet port (220) and outlet port (230) are disposed to be opposed to each other for dividing a flow direction of the culture solution supplied or discharged.

In the culture solution inlet port (220) and outlet port (230) disposed to be adjacent to each other, the culture solution is flowed into the culture solution inlet port (220) which is opened to supply it. The culture solution inlet port (220) and outlet port (230) can be disposed to be adjacent to each other where there is no such possibility.

The gas inlet port (240) may be provided in plural separately from the culture solution inlet port (220) and outlet port (230). In the animal cells cultured in the cell culture flask, $O_2$ supply is needed and $CO_2$ supply is required in the plant cells. These gases can be supplied through the gas inlet port (120). Meanwhile, $N_2$ or other gases can be supplied.

Normal gas supply and discharge is essential to maintain the cell cultured in the cell culture flask in a fresh condition. Therefore, the gas outlet port (250) to discharge the gas supplied inside the cell culture flask to an outside is provided. In a disposable cell culture flask (200), since a predetermined amount of culture solution and gas is supplied to the cell culture flask and then grown cells are harvested, the gas outlet port (250) is not separately needed. In a cell culture flask (200) used repeatedly, the gas outlet port (250) is required to maintain the cells in the fresh condition and an internal portion of the cell culture flask (200) in a clean condition.

The gas outlet port (250) is used to supply the gas excessive or to remove gas generated from the cells per se.

To grow the cells normally, the foreign substance inlet port (260) for supplying a foreign substance can be separately provided. The foreign substance inlet port (260) is provided with a cap-type stopper (265) for opening and closing. The stopper (265) may be a general rubber stopper. The collecting tools such as a pipet can be used where the foreign substance is introduced through the foreign substance inlet port (260).

A user can collect a necessary amount of cells through the foreign substance inlet port (260). The pipet can be also used.

The transparent material includes a transparent plastic such as lexan and acryl or other plastics. Preferably, the transparent material is a non-fragile tempered glass.

The present cell culture flask (200) is formed into the cylindrical shape with a predetermined height comprising the culture space at a center portion thereof. The culture solution inlet ports (220) and outlet ports (230), the gas inlet ports (240) and output ports (250), and the foreign substance inlet port (260) are formed along a side surface of the cell culture flask (200).

This structure represents an example of the cell culture flask. As described above, the cell culture flask may have various structures, e.g., the polyhedral structure.

Figure 8:
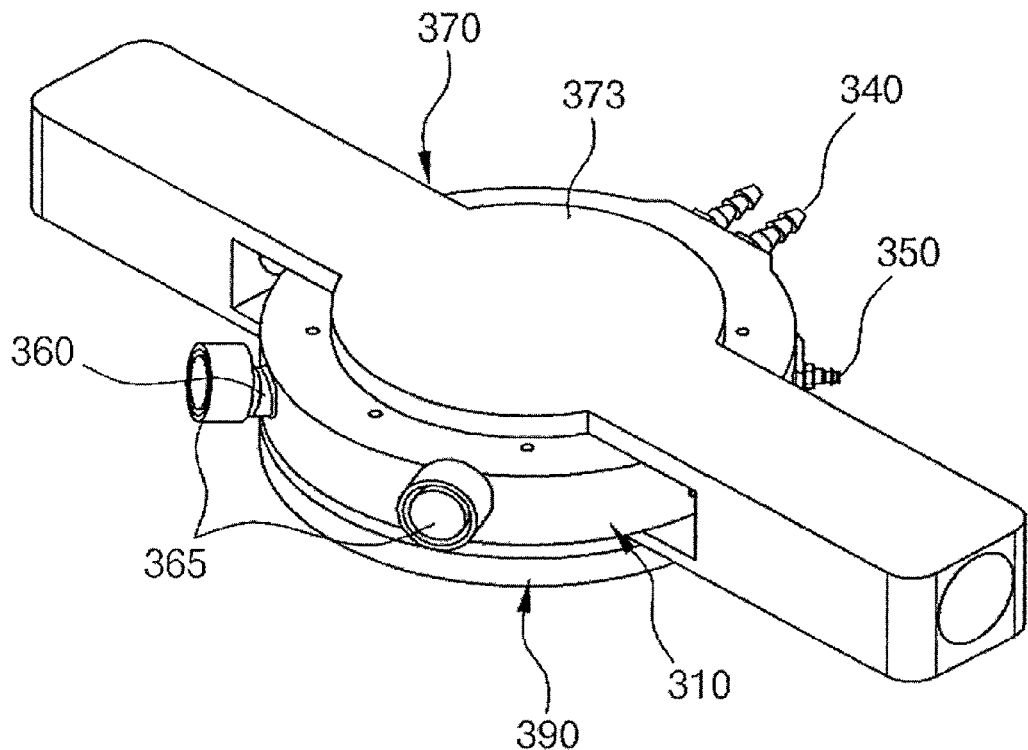
FIG. 8 represents a perspective view of a cell culture device (300) having the cell culture flask (310) of FIG. 1.
Figure 9:
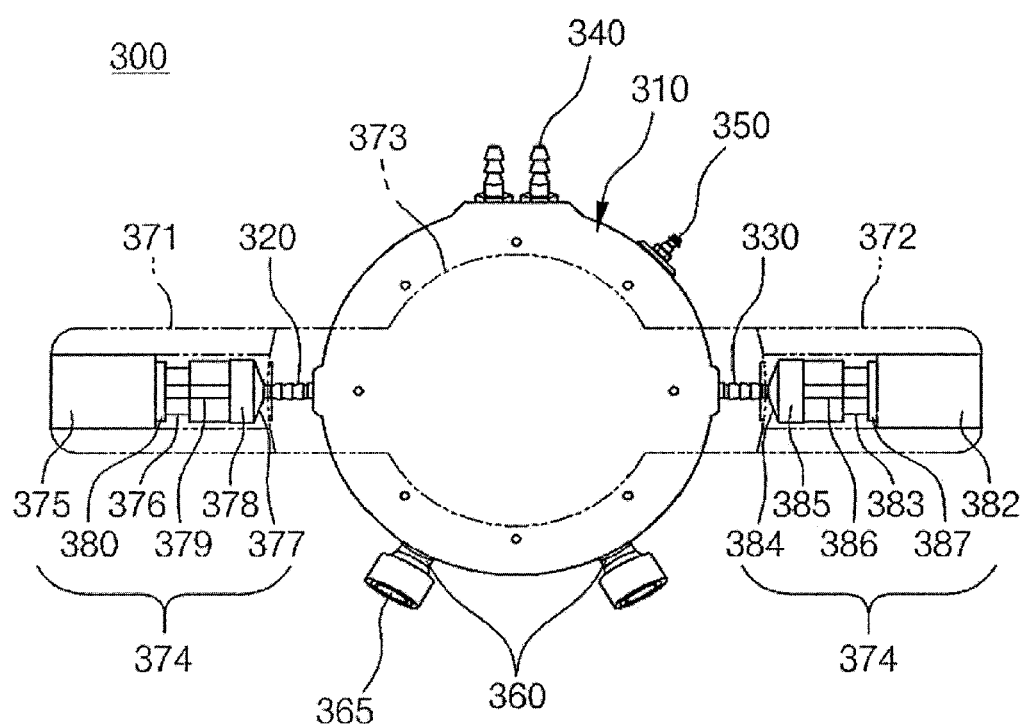
FIG. 9 is a perspective plane view of the cell culture device (300) of FIG. 8.
Figure 10:
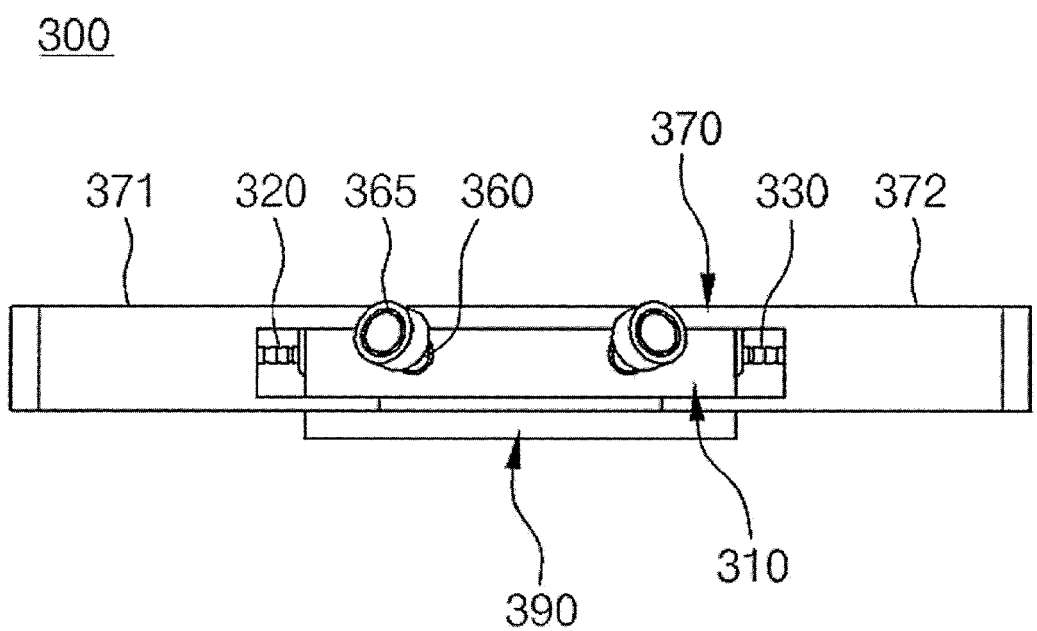
FIG. 10 represents a front view of the cell culture device (300) of FIG. 8.
Figure 11:
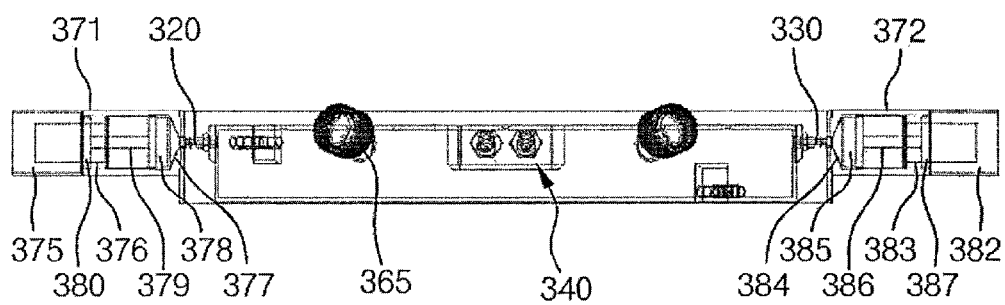
FIG. 11 represents a perspective front view of the cell culture device (300) of FIG. 8.

FIG. 8 represents a perspective view of a cell culture device having the cell culture flask of FIG. 1, and FIG. 9 is a perspective plane view of the cell culture device of FIG. 8. FIG. 10 represents a front view of the cell culture device of FIG. 8, and FIG. 11 represents a stacked status of the cell culture device of FIG. 8.

Given to FIGS. 8-11, a cell culture device (300) with the cell culture flask of the present invention includes a cell culture flask (310) which supplies the culture solution and the gas and cultures the cell, an injection unit (374) for supplying the culture solution to the cell culture flask (310) through its culture solution inlet port (320), a collection unit (381) for collecting the culture solution to an outside of the cell culture flask (310) through its culture solution outlet port (330), and a cell culture flask receiving portion (370) containing the injection unit (374), the collection unit (381) and the cell culture flask (310).

The cell culture device (300) further includes a control part (data not shown) for controlling a supply amount of the gas and the culture solution for the cell culture, various hoses and valves (data not shown) connected with a culture space, a storing part (data not shown) for storing the gas and the culture solution to be supplied and the like. The detailed description thereof will be omitted because these construction elements are used in a conventional cell culture device.

The cell culture flask (310) includes a culture space (data not shown) having a predetermined surface area for culturing cell, a culture solution inlet port (320) for introducing the culture solution or the cell into the culture space, a culture solution outlet port (330) for discharging the culture solution or the cell from the culture space, and a gas inlet port (340) for introducing the various gases into the culture space.

If necessary, the culture solution inlet port (320), the culture solution outlet port (330) and the gas inlet port (340) may be further provided in plural. In addition, the cell culture flask (310) may further includes a gas outlet port (350) for discharging the various gas introduced into the culture space (310), and a foreign substance inlet port (360)

for introducing a foreign substance. If necessary, the gas outlet port (350) and the foreign substance inlet port (360) may be provided in plural.

The foreign substance inlet port (360) is provided with a cap-type stopper (365) for opening and closing. The stopper (365) may be a general rubber stopper. The collecting tools such as a pipet can be used where the foreign substance is introduced through the foreign substance inlet port (360).

A user can collect a necessary amount of cells through the foreign substance inlet port (360). The pipet can be also used.

The present cell culture flask (310) is formed into the cylindrical shape with a predetermined height comprising the culture space at a center portion thereof. The culture solution inlet ports (320) and outlet ports (330), the gas inlet ports (340) and output ports (350), and the foreign substance inlet port (360) are formed along a side surface of the cell culture flask (310). This structure represents an example of the cell culture flask (310). As described above, the cell culture flask (310) may have various structures, e.g., the polyhedral structure.

The cell culture flask (310) is made airtight as a whole and formed of a transparent material to observe its internal portion. Therefore, the researcher can observe a growth level of the cells from the outside.

The transparent material includes a transparent plastic such as lexan and acryl or other plastics. Preferably, the transparent material is a non-fragile tempered glass.

The cell culture flask (310) is airtightly sealed to prevent external contaminants from being infiltrated into the culture space.

As shown in FIG. 9, the injection unit (374) for supplying the culture solution to the cell culture flask (310) and the collection unit (381) for collecting the culture solution from the cell culture flask (310) are formed into an injector. The cell culture device (300) further includes a syringe part (375, 382) having a power supply part (380, 387), a culture solution storing part (376, 383) which is connected with the syringe part (375, 387) and stores the culture solution, a contact part (377, 384) which is connected with the culture solution storing part (376, 383) and contacted with the culture solution inlet port (320) or the culture solution outlet port (330) of the cell culture flask (310) so as to flow the culture solution, a piston member (378, 385) which is disposed to be reciprocated in the culture solution storing part (376, 383), and a connection member (379, 386) of which one end is connected with the piston member (378, 385) and the other end is connected with the power supply part (380, 387).

The injection unit (374) and collection unit (381) can be connected with or separated from the cell culture flask (310) and also detachable with the cell culture flask receiving portion (370). In other words, only the cell culture flask (310) is normally coupled to the cell culture flask receiving portion (370).

For supply or discharge of the culture solution, the injection unit (374) or collection unit (381) is coupled to the injection unit (374) and collection unit (381) of the cell culture flask (310).

The small power supply part (380, 387) operated by electric power supplied through a cable from an outside is provided in the syringe part (375, 382). Furthermore, other units such as an electromotor or a pump are also used as the power supply part (380, 387).

The connection member (379, 386) includes a linear rod which is simply reciprocated, or a lead screw which is reciprocated during rotation. However, it is operated by rotational force of the motor in the lead screw used as the connection member (379, 386).

Instead of using the power supply part like the motor, a user can grasp an outer end portion of the connection member (379, 386) and apply force to move the connection member (379, 386). The user can directly operate the connection member to extract the culture solution or the cells where the purpose of the cell culture is not to produce cells massively, but just to obtain a small amount of particular cells for an experiment.

The culture solution storing part (376, 383) connected with the syringe part (375, 387) stores the culture solution flowed by the piston member (378, 385).

The contact part (377, 384) connected with the culture solution storing part (376, 383) functions as a passage which is contacted with the culture solution inlet port (320) or the culture solution outlet port (330) of the cell culture flask (310) to flow the culture solution.

The contact part (377, 384) is formed into an end part of the syringe (e.g., a funnel) so that a hole through which the culture solution is passed becomes narrow, thereby increasing a flow rate of the culture solution.

It is possible to facilely supply and discharge the culture solution by providing an auto control unit to the injection unit (374) and the collection unit (381), or to the gas inlet port (340) and the gas outlet port (350).

The cell culture flask receiving portion (370) of the cell culture flask (310) represented in FIGS. 8-11 includes an injecting part (371) and a collecting part (372) that the injection unit (374) and the collecting unit (381) are connected thereto, a plate-shaped connecting part (373) which separately connects an upper part or a lower part of the injecting part (371) and the collecting part (372), and a supporting part (390) which is provided at one side of the connecting part (373).

The injecting part (371) and the collecting part (372) of the cell culture flask receiving portion (370) are radially connected with an outer surface of the cell culture flask (310).

And the injecting part (371) and the collecting part (372) of the cell culture flask receiving portion (370) has a structure corresponding to an outer shape of the injection unit (374) and the collection unit (381) to install the injection unit (374) and the collection unit (381).

The plate-shaped connecting part (373) connecting the injecting part (371) and the collecting part (372) is divided into an upper connecting part and a lower connecting part. The connecting part (373) is provided with a circular plate at a center portion thereof where the cell culture flask (310) is disposed between the upper connecting part and the lower connecting part. Since the function of the connecting part (373) is to stably support the cell culture flask (310), it could be other structures such as a rod shape instead of the circular plate shape for supporting.

The supporting part (390) can be further provided at one side of the connecting part (373), i.e., the lower connecting part to support the whole parts of the cell culture device (300). In the cell culture flask (310) with a circular shape, the supporting part (390) may also have a circular structure to protect the whole parts of the cell culture flask (310).

Figure 12:
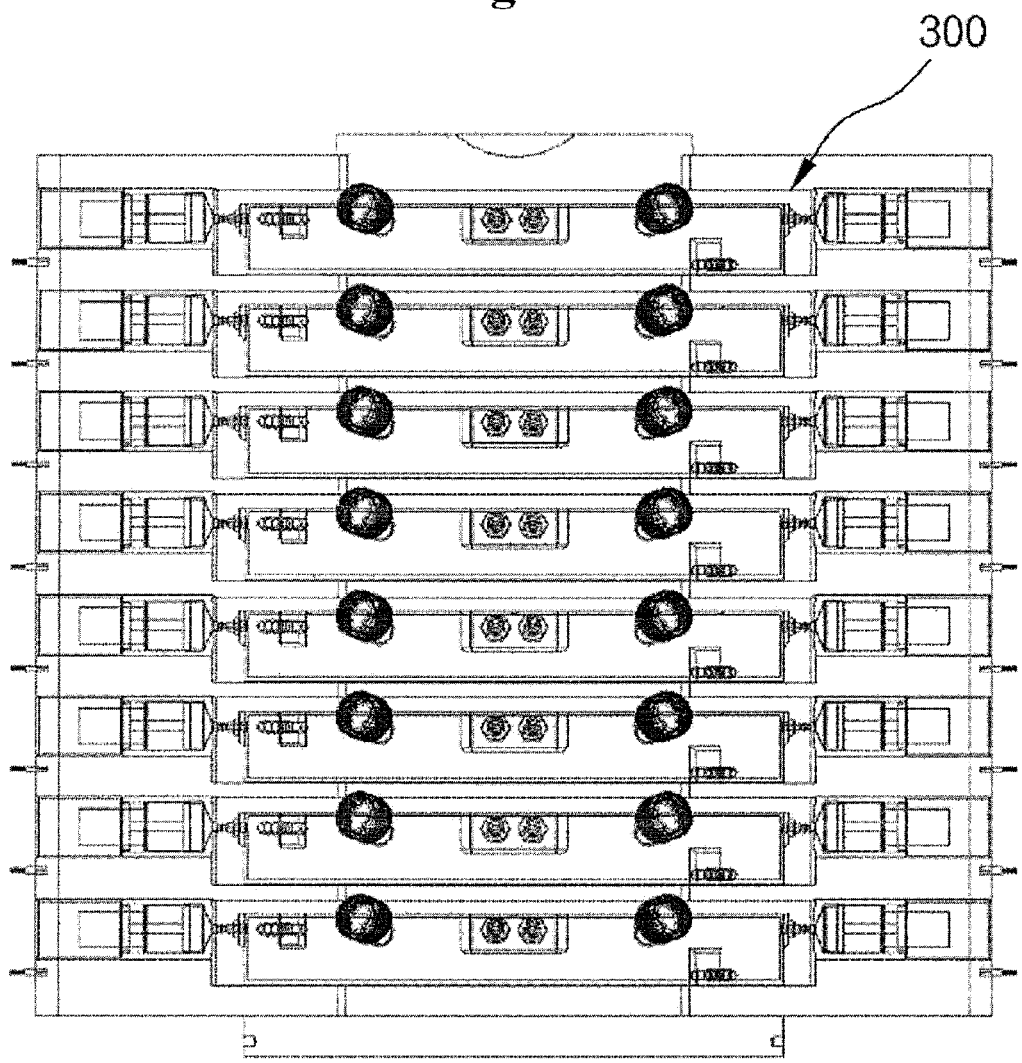
FIG. 12 is a view showing a status that the cell culture devices (300) of FIG. 8 are stacked.

FIG. 12 is a view showing a status that the cell culture devices of FIG. 8 are stacked.

As shown in FIG. 12, each cell culture device (300) is spaced apart from each other by its supporting part (390). Since the supporting part (390) is wide enough to protect the whole parts of the cell culture flask (310), the cell culture devices (300) are stably stacked. As described above, since the cell culture devices (300) are stacked in turn, it is possible to mass-produce the cells.

Figure 13:
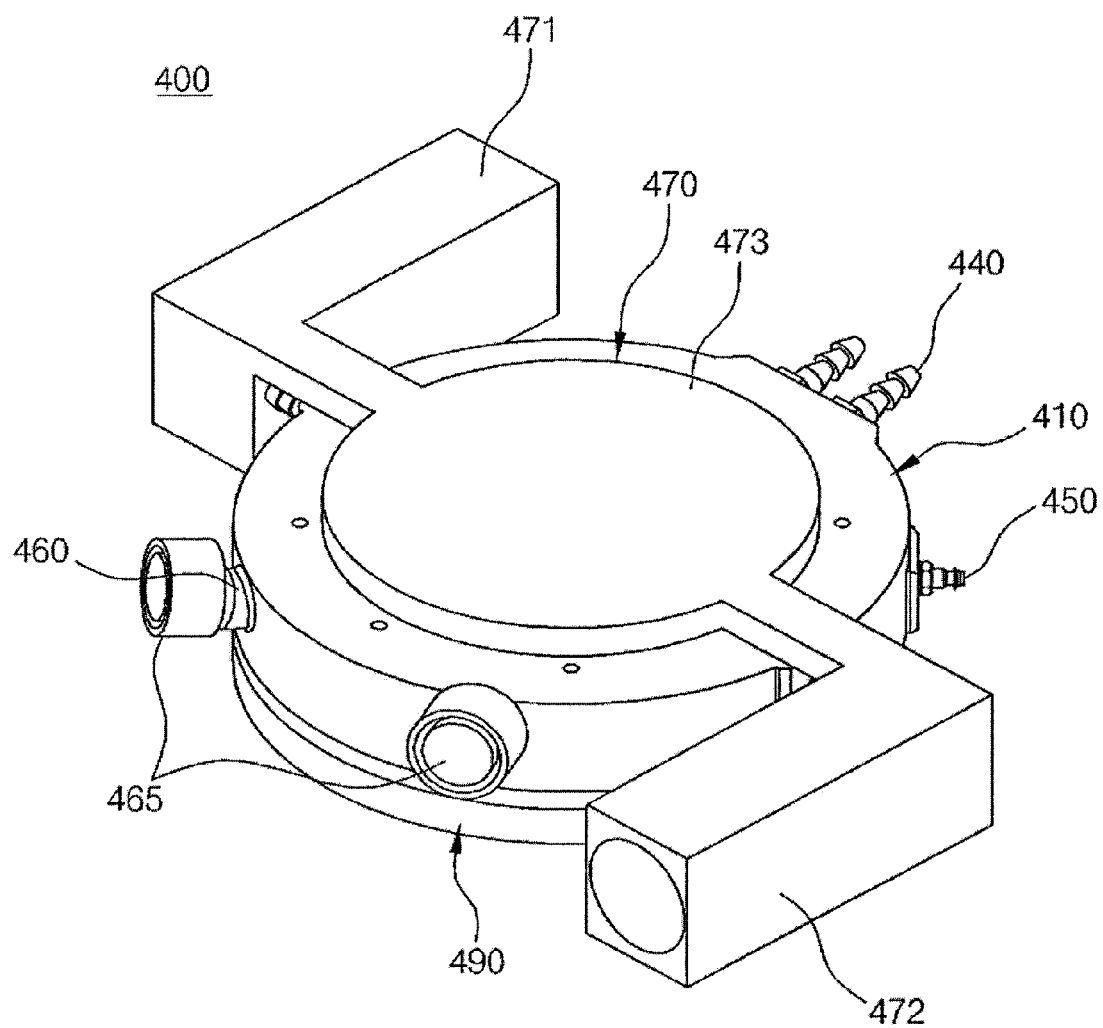
FIG. 13 represents a perspective view of a cell culture device (400) having the cell culture flask (410) of FIG. 1.
Figure 14:
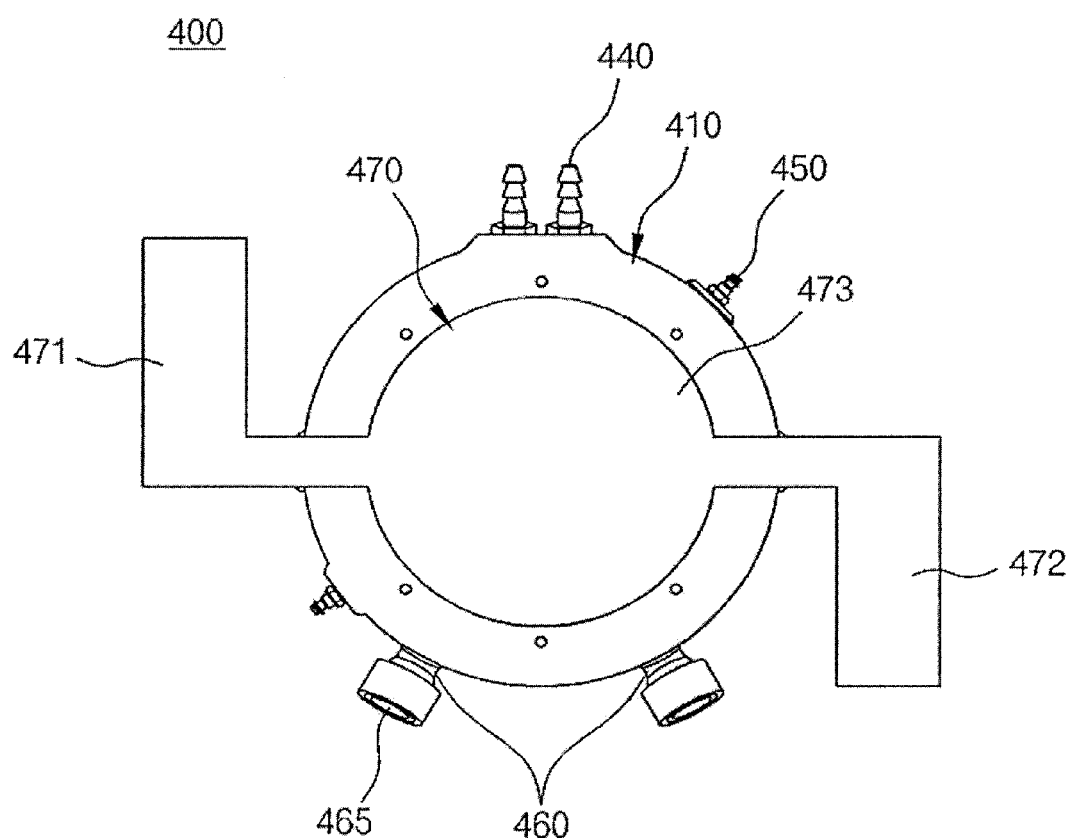
FIG. 14 represents a plane view of the cell culture device (400) of FIG. 13.
Figure 15:
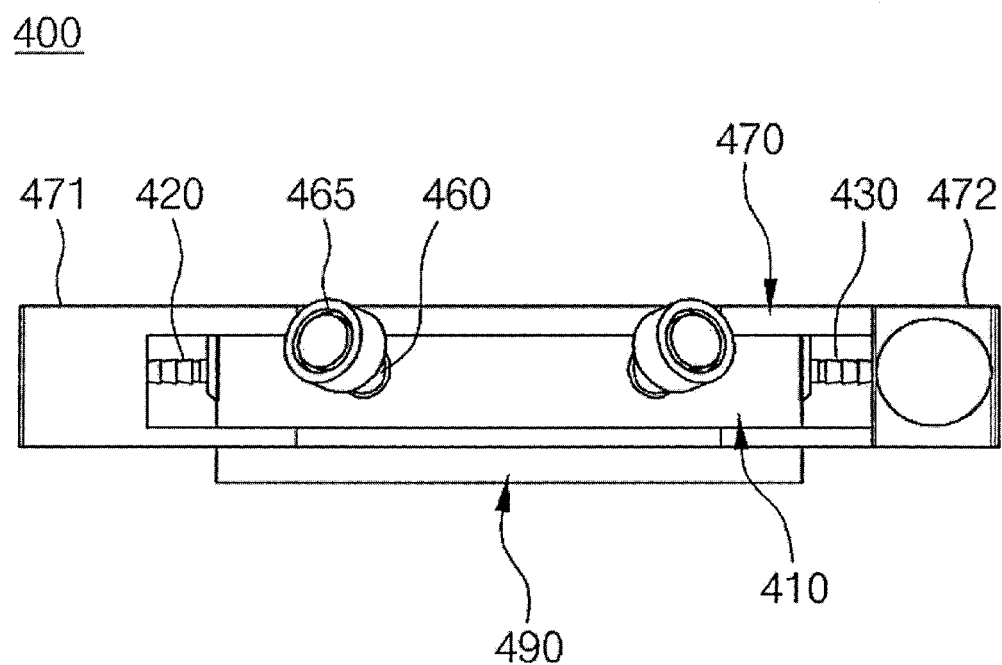
FIG. 15 represents a front view of the cell culture device (400) of FIG. 8.

FIG. 13 represents a perspective view of a cell culture device (400) having the cell culture flask (410) of FIG. 1, FIG. 14 represents a plane view of the cell culture device (400) of FIG. 13, and FIG. 15 represents a front view of the cell culture device (400) of FIG. 13.

The cell culture device further includes a control part (data not shown) for controlling a supply amount of the gas and the culture solution for the cell culture, various hoses and valves (data not shown) connected with a culture space, a storing part (data not shown) for storing the gas and the culture solution to be supplied and the like. The detailed description thereof will be omitted because these construction elements are used in a conventional cell culture device.

As represented in FIGS. 13-15, an injecting part (471) and a collecting part (472) of a cell culture flask receiving portion (470) are vertically connected with an outer surface of a cell culture flask (410).

Preferably, a culture solution inlet port (420) and a culture solution outlet port (430) of the cell culture flask (410) may be formed of a form to be vertically bent so that an injection unit and a collection unit are detachable with the cell culture flask (410) in an easy manner.

According to the present invention, the cell culture flask receiving portion (370, 470) may be formed of a transparent material such as lexan and acryl to observe a growth level of the cells from the outside. Alternatively, the cell culture flask receiving portion (370, 470) may be constituted as a stainless steel to prevent corrosions by external contaminants or damages by external impacts.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A cell culture device, comprising:
   (a) cell culture flasks for culturing a cell using a culture solution and various gases, each of the cell culture flasks comprising: (i) a culture space with a predetermined area for culturing the cell; (ii) one or more culture solution inlet ports for introducing the culture solution or the cell into the culture space; (iii) one or more culture solution outlet ports for discharging the culture solution or the cell supplied to the culture space; (iv) one or more gas inlet ports for introducing the various gases into the culture space; (v) one or more gas outlet ports for discharging the various gases supplied to the culture space; and (vi) one or more foreign substance inlet ports for introducing a foreign substance;
   wherein the one or more culture solution inlet ports and the one or more culture solution outlet ports are formed to be protruded from an outer surface of the cell culture flasks and to constitute a narrow end;
   wherein the one or more gas inlet ports and the one or more gas outlet ports are formed to be protruded from an outer surface of the cell culture flasks;
   wherein the one or more foreign substance inlet ports are formed to be protruded from an outer surface of the cell culture flasks and formed into a cylindrical shape;
   wherein each of the cell culture flasks is formed into a cylindrical shape with a predetermined height and comprises the culture space at a center portion thereof, and all ports are formed along a side surface of the cell culture flask in order of the one or more culture solution inlet ports, the one or more gas inlet and output ports, the one or more culture solution outlet ports, and the one or more foreign substance inlet ports;
   wherein each of the one or more culture solution inlet ports and the one or more culture solution outlet ports comprises (i) a cylindrical tube member which is outwardly protruded to receive the culture solution and formed with a side surface hole through which the culture solution is flowed, (ii) a piston member which is disposed to be reciprocated in the cylindrical tube member, (iii) a connection member of which one end is connected with the piston member and the other end is connected with an external power supply, being formed into a linear rod or a lead screw; and (iv) a sealing member which is attached to an end of the cylindrical tube member and formed into a cylindrical shape with an opening through which the connection member can be reciprocated;
   wherein the cell culture flasks are made airtight and formed of a transparent material so that a user can see an internal portion of the cell culture flasks;
   wherein the cell culture flasks are stacked vertically;
   (b) injection units for supplying the culture solution to the cell culture flasks through the one or more culture solution inlet ports of the cell culture flasks, and collection units for collecting the culture solution to outside of the cell culture flasks through the one or more culture solution outlet ports of the cell culture flasks;
   wherein each of the infection units and the collection units is formed into an injector as a whole;
   (c) cell culture flask receiving portions, each of the cell culture flask receiving portions comprising an injecting part and a collecting part comprising one or more of the injection units and one or more of the collecting units, respectively, a plate-shaped connecting part which separately connects an upper part or a lower part of the collecting part and the injecting part, and a support which is provided at the connecting part; and
   wherein each of the cell culture flasks is disposed between the upper part and the lower part of one of the connecting parts of a cell culture flask receiving portion, and wherein the injecting part and the collecting part of each of the cell culture flask receiving portions are connected with the connecting part of a cell culture flask receiving portion in the opposite direction.

2. The cell culture device according to claim 1, wherein the one or more foreign substance inlet ports are opened and closed by cylindrical stoppers.

3. The cell culture device according to claim 1, wherein the transparent material comprises a plastic or a tempered glass.

4. The cell culture device according to claim 1, wherein the power supply comprises a detachable motor which is operated by electric power supplied through a cable from an outside.

5. The cell culture device according to claim 1, wherein the injecting part and the collecting part of one or more of the cell culture flask receiving portions are radially or vertically connected with an outer surface of the respective one or more cell culture flask receiving portions.

6. The cell culture device according to claim 1, wherein the one or more cell culture flask receiving portions are formed of a plastic or a stainless steel.

* * * * *